United States Patent
Zahedi et al.

(10) Patent No.: US 10,285,827 B2
(45) Date of Patent: May 14, 2019

(54) LOWER LIMB PROSTHESIS WITH KNEE FLEXION CONTROL DURING DESCENT OF A DOWNWARD INCLINE

(71) Applicant: BLATCHFORD PRODUCTS LIMITED, Basingstoke, Hampshire (GB)

(72) Inventors: Mir Saeed Zahedi, London (GB); Nadine Stech, Hampshire (GB); David Moser, Southampton (GB); Andrew John Sykes, Surrey (GB)

(73) Assignee: Blatchford Products Limited, Hampshire (GB)

( * ) Notice: Subject to any disclaimer, the term of this patent is extended or adjusted under 35 U.S.C. 154(b) by 0 days.

(21) Appl. No.: 14/364,637

(22) PCT Filed: Dec. 12, 2012

(86) PCT No.: PCT/GB2012/053106
§ 371 (c)(1),
(2) Date: Jun. 11, 2014

(87) PCT Pub. No.: WO2013/088142
PCT Pub. Date: Jun. 20, 2013

(65) Prior Publication Data
US 2014/0379096 A1 Dec. 25, 2014

Related U.S. Application Data

(60) Provisional application No. 61/580,887, filed on Dec. 28, 2011, provisional application No. 61/647,016, filed on May 15, 2012.

(30) Foreign Application Priority Data

Dec. 13, 2011 (GB) .................................. 1121437.6
May 14, 2012 (GB) .................................. 1208410.9

(51) Int. Cl.
*A61F 2/64* (2006.01)
*A61F 2/66* (2006.01)
(Continued)

(52) U.S. Cl.
CPC .................. *A61F 2/68* (2013.01); *A61F 2/64* (2013.01); *A61F 2/66* (2013.01); *A61F 2/6607* (2013.01);
(Continued)

(58) Field of Classification Search
CPC ............. A61F 2/64; A61F 2/642; A61F 2/644
See application file for complete search history.

(56) References Cited

U.S. PATENT DOCUMENTS 6,517,585 B1 * 2/2003 Zahedi ...................... A61F 2/68
623/24
7,811,333 B2 * 10/2010 Jonsson ................ A61F 2/6607
623/24
(Continued)

FOREIGN PATENT DOCUMENTS

EP    1 334 891 A2    8/2008
GB    2 280 609 A     2/1995
(Continued)

OTHER PUBLICATIONS

Motoda et al., English machine translation for Japanese publication No. JP 2005-230207 A, Feb. 9, 2005.*
(Continued)

*Primary Examiner* — Marcia L Watkins
(74) *Attorney, Agent, or Firm* — Alston & Bird LLP

(57) ABSTRACT

A lower limb prosthesis comprises an attachment section (10), a shin section (12), a foot section (14), a knee joint (16) pivotally connecting the attachment section (10) and the shin section (12), and an ankle joint (22) pivotally connecting the shin section (12) and the foot section (14). The knee joint
(Continued)

includes a dynamically adjustable knee flexion control device (18) for damping knee flexion. The prosthesis further comprises a plurality of sensors (52, 53, 54, 85, 87) each arranged to generate sensor signals indicative of at least one respective kinetic or kinematic parameter of locomotion or of walking environment, and an electronic control system (100) coupled to the sensors (52, 53, 54, 85, 87) and to the knee flexion control device (18) in order dynamically and automatically to modify the flexion control setting of the knee joint (16) in response to signals from the sensors. When the inclination sensor signals indicate descent of a downward incline, the damping resistance of the knee flexion control device (18) is set to a first level during a major part of the stance phase of the gait cycle and to a second, lower level during a major part of the swing phase of the gait cycle. During an interval including a latter part of the stance phase, the knee flexion control device (18) is adjusted so that the damping resistance to knee flexion is between the first and second levels.

23 Claims, 16 Drawing Sheets

(51) Int. Cl.
*A61F 2/74* (2006.01)
*A61F 2/68* (2006.01)
*A61F 2/70* (2006.01)
*A61F 2/50* (2006.01)
*A61F 2/76* (2006.01)

(52) U.S. Cl.
CPC ............. *A61F 2002/5003* (2013.01); *A61F 2002/5006* (2013.01); *A61F 2002/5033* (2013.01); *A61F 2002/701* (2013.01); *A61F 2002/704* (2013.01); *A61F 2002/74* (2013.01); *A61F 2002/741* (2013.01); *A61F 2002/745* (2013.01); *A61F 2002/747* (2013.01); *A61F 2002/748* (2013.01); *A61F 2002/764* (2013.01); *A61F 2002/7625* (2013.01); *A61F 2002/7635* (2013.01); *A61F 2002/7645* (2013.01)

(56) References Cited

U.S. PATENT DOCUMENTS

| | | | | |
|---|---|---|---|---|
| 8,598,815 B2* | 12/2013 | Glaister | .................. | A61F 2/66 318/139 |
| 2005/0070834 A1 | 3/2005 | Herr et al. | | |
| 2007/0050045 A1* | 3/2007 | Clausen | .................. | A61F 2/66 623/24 |
| 2009/0054996 A1 | 2/2009 | Sykes et al. | | |
| 2009/0222105 A1 | 9/2009 | Clausen | | |
| 2009/0265018 A1 | 10/2009 | Goldfarb et al. | | |
| 2011/0202144 A1* | 8/2011 | Palmer | .................. | A61B 5/1114 623/39 |
| 2011/0230975 A1 | 9/2011 | Moser et al. | | |
| 2012/0226364 A1* | 9/2012 | Kampas | .................. | A61F 2/64 623/24 |

FOREIGN PATENT DOCUMENTS

| | | |
|---|---|---|
| GB | 2 328 160 A | 2/1999 |
| GB | 2 334 891 A | 9/1999 |
| GB | 2 367 753 A | 4/2002 |
| JP | 2001-514925 A | 9/2001 |
| JP | 2004-167106 A | 6/2004 |
| JP | 2004-167107 A | 6/2004 |
| JP | 2005-230207 A | 9/2005 |
| JP | 2007-068627 A | 3/2007 |
| WO | WO 99/08621 A2 | 2/1999 |
| WO | WO 01/43669 A1 | 6/2001 |
| WO | WO 2007/110585 A2 | 10/2007 |
| WO | WO 2008/103917 A1 | 8/2008 |
| WO | WO 2010/085287 A2 | 7/2010 |

OTHER PUBLICATIONS

International Search Report and Written Opinion for Application No. PCT/GB2012/053106 dated Aug. 5, 2013.
Search Report for Application No. GB 1208410.9 dated Aug. 23, 2012.
Search Report for Application No. GB 1121437.6 dated Mar. 27, 2012.
Search Report for Application No. GB 1121437.6 dated Jul. 20, 2012.
Search Report for Application No. GB 1121437.6 dated Jul. 23, 2012 (Claims 26-29).
Search Report for Application No. GB 1121437.6 dated Jul. 23, 2012 (Claim 32).
Notification of Reason for Rejection from corresponding Japanese Patent Application No. 2014-546632 dispatched Oct. 25, 2016.
Examination Report for Great Britain Application No. GB1208410.9 dated Mar. 27, 2017.
Winter, David A.; Kinematics 1.3.2 and Kinetics 1.3.3; Biomechanics and Motor Control of Human Movement, Fourth Edition; 2009; 3 pages.

* cited by examiner

|  | Knee Hydraulic $ stance | Knee Hydraulic $ swing | Knee Pneumatic # | Foot Plantarflexion | Foot Dorsiflexion |
|---|---|---|---|---|---|
| Ramp up* | H | L | L,M,H | H or M | L or M |
| Ramp down* | H,M | L,M,H | L,M,H | L or M | H or M |
| Level Velocity* | H | L | L,M,H | L,M,H | L,M,H |
| Stairs down | H | H | H | M | M |
| Stand Relaxed | H or VH | - | H | Leave chosen setting when on slope else M or H | Leave Chosen setting when on slope else M or H |
| Sitting | H | H | L | M | M |

Fig. 4A

| Ramp up | Knee Hydraulic $ stance | Knee Hydraulic $ swing | Knee Pneumatic # | Foot Plantarflexion | Foot Dorsiflexion |
|---|---|---|---|---|---|
| Ramp up Transition - slow velocity | H | L | L | M/H- or M+ | M/L+ or M- |
| Ramp up Transition - medium velocity | H | L | M | M/H | M/L |
| Ramp up Transition - fast velocity | H | L | H | M/H+ or H- | M/L- or L+ |
| Ramp up - slow velocity | H | L | L | H- or M/H | M/L- or L+ |
| Ramp up - medium velocity | H | L | M | H | L |
| Ramp up - fast velocity | H | L | H | H+ or VH | L- or VL |
| Steep ramp up - slow velocity | H | L | L | H or H+ | L or L+ |
| Steep ramp up - medium velocity | H | L | M | H or VH | L or VL |
| Steep ramp up - fast velocity | H | L | H | VH or VH+ | VL or VL- |

Fig. 4B

| Ramp down | Knee Hydraulic $ stance | Knee Hydraulic $ swing | Knee Pneumatic # | Foot Plantarflexion | Foot Dorsiflexion |
|---|---|---|---|---|---|
| Ramp down Transition - slow velocity | H,M | L,M | L | M/L+ or M- | M/H- or M+ |
| Ramp down Transition - medium velocity | H,M | L,M | M | M/L | M/H |
| Ramp down Transition - fast velocity | H,M | L,M | H | M/L- or L+ | M/H+ or H- |
| Ramp down - slow velocity | H or H-,M | L,M | L | M/L- or L+ | H- or M/H |
| Ramp down - medium velocity | H or H-,M | L,M | M | L | H |
| Ramp down - fast velocity | H or H-,M | L,M | H | L- or VL | H+ or VH |
| Steep ramp down - slow velocity | H | H | L | L or L+ | H or H+ |
| Steep ramp down - medium velocity | H | H | M | L or VL | H or VH |
| Steep ramp down - fast velocity | H | H | H | VL or VL- | VH or VH+ |

Fig. 4C

| Velocity - Level Walk | Knee Hydraulic $ stance | Knee Hydraulic $ swing | Knee Pneumatic # | Foot Plantarflexion | Foot Dorsiflexion |
|---|---|---|---|---|---|
| Slow speed level walking | H | L | L | L or M | H or M |
| Medium speed level walking | H | L | M | M | M |
| Fast speed level walking | H | L | H | H | L |
| Very fast speed level walking | M or H | L or M | H or VH | H or VH | L or VL |

Fig. 4D

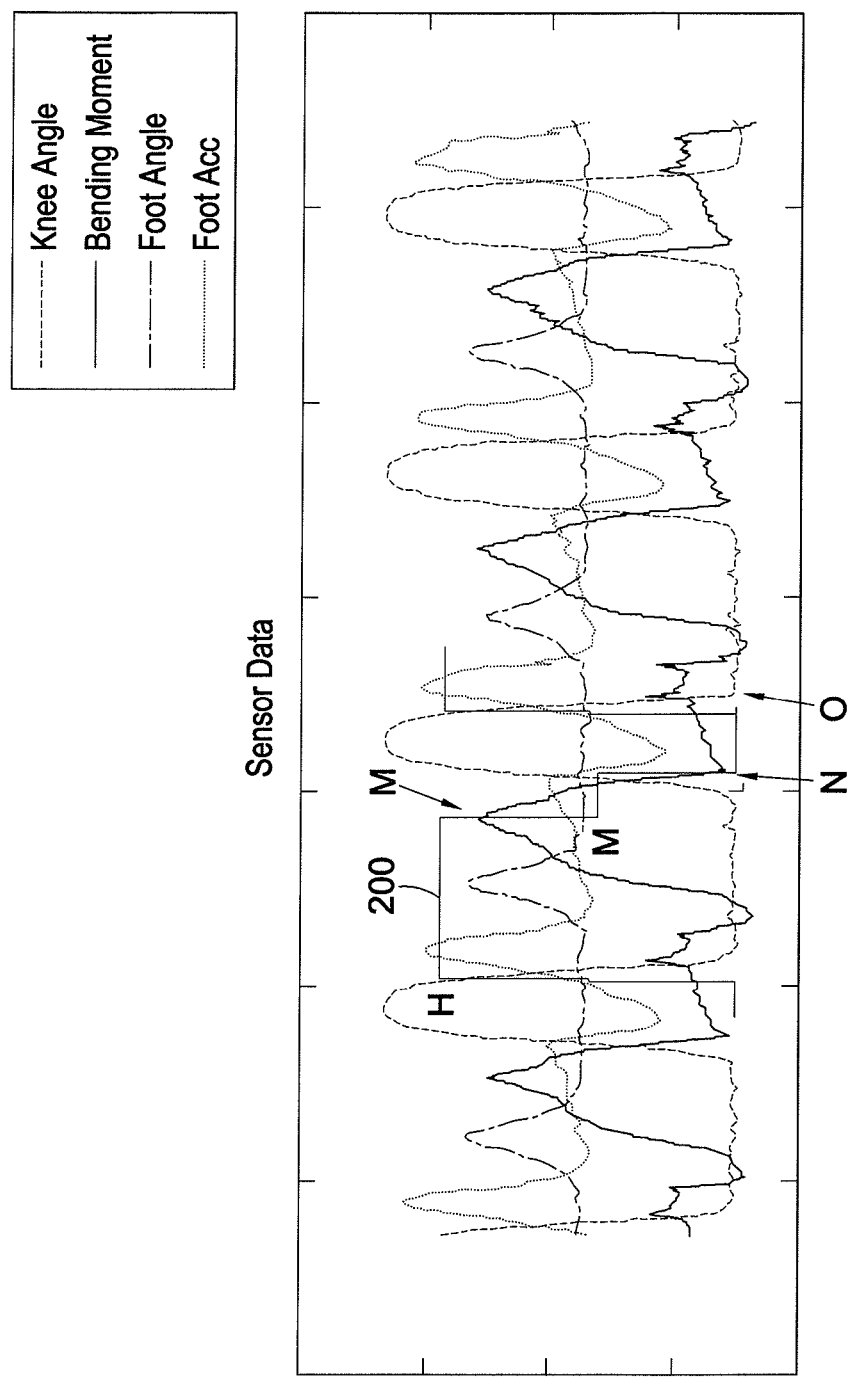

LOWER LIMB PROSTHESIS WITH KNEE FLEXION CONTROL DURING DESCENT OF A DOWNWARD INCLINE

CROSS-REFERENCE TO RELATED APPLICATIONS

This application is a national stage application filed under 35 U.S.C. 371 of International Application No. PCT/GB2012/053106, filed Dec. 12, 2012, which claims priority from GB 1121437.6, filed Dec. 13, 2011; Provisional Application No. 61/580,887, filed Dec. 28, 2011; GB 1208410.9, filed May 14, 2012; and Provisional Application No. 61/647,016, filed May 15, 2012, each of which is incorporated by reference herein in its entirety.

This invention relates to a lower limb prosthesis including a knee joint and an ankle joint. Both the knee joint and the ankle joint include respective flexion control devices actuated by an electronic control system.

Known lower limb prostheses for above-knee amputees include prostheses with adaptive control systems for controlling knee flexion during both stance and swing phases of the walking cycle. Such a prosthesis is disclosed in WO99/08621. In this example, the control system includes sensors for sensing shin bending moment and knee flexion angle, corresponding electrical signals being fed to a processing circuit for automatically adjusting hydraulic and pneumatic flexion control devices. Knee flexion is controlled in the stance phase in response to the activity mode of the amputee, i.e. in response to changes between level walking, walking uphill, and walking downhill, and in the swing phase in response to walking speed. The disclosure of WO99/08621 is incorporated herein by reference.

It is also known to provide dynamically variable damping of a prosthetic ankle joint as in, for example, WO2008/103917 and related U.S. application Ser. No. 13/150,694 filed Jun. 1, 2011, the disclosure of which is incorporated herein by reference. In this example, the ankle joint includes an hydraulic piston and cylinder assembly providing independent variation of damping resistance in dorsi-flexion and plantar-flexion directions in response to, e.g., ground inclination.

It is an object of the present invention to provide above-knee amputees with an electronically controlled prosthesis with improved limb function in a wide range of conditions.

According to a first aspect of the invention, a lower limb prosthesis comprises an attachment section, a shin section, a foot section, a knee joint linking the attachment section and the shin section, and an ankle joint linking the shin section and foot section, wherein the knee joint includes a knee flexion control device and the ankle joint includes an ankle flexion control device, the prosthesis further comprising at least one sensor associated with the knee joint and at least one sensor associated with the ankle joint, each such sensor being arranged to generate sensor signals indicative of at least one respective kinetic or kinematic parameter of activity or locomotion, or of walking environment, wherein the prosthesis further comprises an electronic control system coupled to the said sensors to receive the sensor signals and to the flexion control devices to feed control signals to the said control devices in order dynamically and automatically to modify the flexion control settings of the knee joint and the ankle joint in response to the sensor signals, and wherein the arrangement of the sensors, the control devices and the electronic control system is such that, during locomotion, the flexion control settings of the knee joint and those of the ankle joint are each determined jointly by the sensor signals from the sensor or sensors associated with the knee joint and the sensor signals from the sensor or sensors associated with the ankle joint. In this way, it is possible to provide a lower limb prosthesis for an above-knee or through-knee disarticulation amputee with integrated microprocessor control. In particular, the limb may combine microprocessor control of a hybrid hydraulic, yielding stance and pneumatic swing control device in the knee together with hydraulic control and dorsi-flexion damping (and, preferably, plantar-flexion damping) of the ankle joint, bringing advantages in terms of coordinated adjustment at both knee and ankle levels based on signals from sensors placed at optimum positions within the prosthesis, according to the respective sensed parameters. References to "flexion control" in this specification are to be interpreted in the general sense of including control of flexion and/or extension (rather than merely in the sense of increasing bending of a joint).

Integration of the control functions for the knee joint and the ankle joint, using inputs from sensors at the level of the knee and the level of the ankle, allows more accurate measurement of kinetic and kinematic parameters associated with locomotion. For instance, sensors at the level of the ankle joint or foot are best suited to detecting changes in surface inclination whereas sensors associated with the knee joint are best suited for sensing certain velocity and period parameters.

Integrated control may be achieved in a prosthesis with, for instance, fibre-reinforced composite leaf springs, and axial springs for absorbing mechanical energy, for improved function on a variety of terrains and at different speeds of locomotion.

In one embodiment of the invention, the prosthesis has a sensor associated with the ankle joint for generating a sensor signal indicative of a shin or ankle bending moment, the arrangement of the sensors, the control devices and the electronic control system being such that, during locomotion, the flexion control settings of the knee joint are adjusted in response to the shin or ankle bending moment. Alternatively, or in addition, the prosthesis may have a sensor associated with the ankle joint in the form of an accelerometer mounted, e.g., on the prosthetic foot section, the flexion control settings of the knee joint being adjusted in response to signals from the accelerometer.

The arrangement is preferably such that, during locomotion, the flexion control settings of the knee joint are determined in response to settings of the ankle flexion control device, the latter being a damping device providing variable damping resistance. Signals representative of walking speed, e.g. signals representative of stride length and/or step rate, may be generated in the electronic control system in response to sensor signals from the sensor or sensors associated with the knee joint and the sensor signals from the sensor or sensors associated with the ankle joint. Generally, the arrangement is such that the flexion control settings of the ankle joint are determined in response to such walking speed signals.

Additionally, in the preferred prosthesis, the flexion control settings of the knee joint are modified in response to sensor signals indicative of ground inclination, such signals being derived from an accelerometer associated with the ankle joint. Indeed, the flexion control settings of the knee joint may be modified in response to a combination of sensor signals representative of both ground inclination and the flexion control settings of the ankle joint. It is preferred that control device settings effective to control flexion resistance at the knee during both the stance phase and the swing phase are adjusted in response to sensed walking speed.

A gyroscopic sensor may be mounted, for instance, on the shin section, i.e. at a location between the knee joint axis and the ankle joint axis. Alternatively, the gyroscope sensor may be mounted in the sagittal plane on the socket, or on the knee above the knee joint axis, or below the ankle joint axis, e.g. on the foot. The sensor measures angular velocity.

Other sensors forming part of the prosthesis may include at least one sensor measuring real time loads, e.g. externally applied bending moments and/or axial forces. Such sensors may be strain gauges. Shear forces on the foot components may be measured in this way using strain gauges in the foot. Shear forces in the shin may be measured, e.g. by strain gauges at the knee level, typically on the upper part of the shin, such as on a shin cradle connecting knee joint components to a shin tube. Sensors may also be included to detect both linear displacement and angular motion at the knee and at the ankle/foot level. Where velocity, orientation or acceleration measurements are required, accelerometers and gyroscopic sensors are preferred. Such measurements may be used to detect different environments, such as ramps and stairs, as well as predicting changes in speed of locomotion, changes in stride length and events such as coming to a standstill, sitting down, starting and stopping locomotion, turning and manoeuvring around obstacles.

Thus, the arrangement of the preferred electronic control system allows definition of a climbing stairs mode. The sensors may include an ankle angle sensor and a knee angle sensor, the system being further arranged such that the climbing stairs mode is activated when signals from the ankle angle sensor and the knee angle sensor are indicative of the ankle joint being dorsi-flexed beyond a first dorsi-flexion threshold in conjunction with the knee joint being flexed beyond a first knee flexion threshold.

Other activity modes may further comprise fast and slow walking modes and a descending stairs mode.

The arrangement of the sensors, the control devices and the electronic control system is preferably such that the flexion control settings of the knee joint are responsive to activity mode. Similarly, the flexion control settings of the ankle joint may be responsive to activity mode.

Typically, the flexion control settings of the knee joint and those of the ankle joint are responsive to sensor signals indicative of shin bending moment, knee flexion angle, ankle flexion angle, and ground inclination. Signals indicative of stride length and angular velocity may also be used.

The arrangement may also be such that, during locomotion, the flexion control settings of the ankle joint are modified to achieve a predetermined shin bending moment profile, preferably one in which, during the stance phase of the gait cycle, a graph plotting bending moment with time has a stepped shape. More than one preferred bending moment profile can be used, depending on, e.g., activity mode, a detected gait parameter such as walking speed or stride length, or ground inclination. The stepped shape of the bending moment profile is characterised by a first period in which the bending moment increases with a first gradient, followed by a second period in which the moment increases with a second gradient which is less than the first gradient, followed by a third period in which the gradient reverts to a level similar to that of the first period, the arrangement being such that if the bending moment profile does not exhibit the said stepped shape, the stance phase plantar-flexion resistance of the ankle flexion control device is increased and/or the stance phase dorsi-flexion resistance of the ankle flexion control device is decreased. Typically, the duration of the third period of the stepped bending moment profile shape is at least half, preferably at least 80 percent of that of the second period. The control settings may be adjusted to achieve different bending moments for different activities including, for instance, ground inclination, step rate or stride length.

In the case of the prosthesis including an ankle flexion angle sensor, the control system may be arranged such that, if the area under the dorsi-flexion curve with respect to time during the stance phase exceeds a respective predetermined area threshold, the stance phase plantar-flexion resistance of the ankle flexion control device is increased and/or the stance phase dorsi-flexion resistance of the ankle flexion control device is decreased.

The arrangement may be such that the plantar-flexion and dorsi-flexion resistance at the ankle are dynamically and automatically adjusted during locomotion to cause the shin bending moment profile to exhibit a step-shaped increase during the stance phase and/or to reduce the ankle dorsi-flexion amplitude during the stance phase.

Modifications or adjustments of the ankle joint flexion resistance or resistances are typically performed in a calibration mode of the electronic control system, thereby to establish flexion resistance settings which are used during subsequent locomotion in response to sensor output signals representative of the above-mentioned kinetic or kinematic parameter or parameters of locomotion, or of walking environment.

With regard to the composition of the electronic control system, a single microprocessor controller may be used or there may be a central controller and one or more subsidiary controllers. At least one of such controllers receives signals from the sensors, the respective measured parameters being used to define activity modes, such as level walking, walking up a ramp, walking down a ramp, fast walking, slow walking, etc., as input values to a multiple-layer matrix containing control output values to form the basis for selected output signals for setting mechanical control devices in the knee joint and ankle joint. Combinations of such modes are allowed by the multi-layer matrix. The activity mode may distinguish between stride length and step rate, given that any particular speed of locomotion may be achieved by the combination of a low step rate and a large stride length or that of a high step rate and a small stride length. Activity modes may, therefore, include slow short steps, fast short steps, slow long steps, and fast long steps. Starting and stopping steps may also be sensed and taken into account. In particular, each activity mode, detected by processing the sensor signals, has associated matrix values defining ankle joint and knee joint flexion resistance settings pre-selected for that mode. In the preferred prosthesis, the settings relate to hydraulic and pneumatic control devices for the knee joint, controlling flexion resistance in the stance phase and swing phase respectively, and a control device or devices for resisting plantar- and dorsi-flexion of the ankle joint. Such devices may comprise linear or rotary pistons or vanes which are reciprocable in chambers containing a fluid medium, whether liquid or gas. Valves and motors allow damping to be varied by controlling the flow of fluid and, thereby, the movement of the piston and vane in each case.

Settings are preferably established during a teaching or calibration mode which may be under the control of a prosthetist or are carried out according to an automatic calibration process. EP2334891 and WO2007/110585 disclose techniques for setting swing phase resistance automatically. The disclosures of these published patent applications and equivalent U.S. application Ser. No. 12/282,541 filed Sep. 11, 2008 are expressly incorporated in the present application by reference.

During the calibration mode, individual locomotion characteristics are detected and optimum values for, e.g., stance yield (flexion resistance), the degree of heel rise during the swing phase, the degree of plantar-flexion resistance and dorsi-flexion resistance at preferred walking speeds and terrain conditions are established. This calibration data can be refined further in an automatic manner through manual adjustment via input commands to the electronic control system using interface switches or via wireless or wired remote control.

In the preferred prosthesis, the control system adjusts the control device settings according to activity mode in order to achieve safe yield control of the knee joint as it is being loaded, optimum release of the yield to initiate swing with minimum user effort, and correct braking of the ankle joint to enable natural movement and progression of the centre of mass of the amputee. Both plantar-flexion and dorsi-flexion are damped according to activity mode, to maximise the propulsion push-off force from energy-storing elements of the prosthesis so that an energy-efficient, safe and comfortable movement is provided for the user. Initially, settings are established for level walking at a preferred walking speed. The level of compensation and abnormal adjustment by the user is minimised as far as possible so as to give the perception of being pushed or assisted forward, the limb braking or assisting to control speed in as natural a manner as possible as the prosthesis strikes the ground. The matrix values established for level walking at the preferred walking speed are then adjusted to provide new matrix values for slopes, different speeds, and non-walking modes. In the preferred prosthesis, the sensors and the remainder of the control system can detect and distinguish between ascending and descending ramps, the degree of inclination of the ramps, ascending and descending stairs, the speed of ascent or descent, the speed of walking from the slowest the amputee walks to the fastest, as well as sitting, standing-up from chairs, and other modes such as maneuvering to avoid an obstacle. The matrix has a number of matrix levels, at least one for each activity mode.

According to a second aspect of the invention, there is provided a lower limb prosthesis comprising an attachment section, a shin section, a foot section, a knee joint linking the attachment section and the shin section, and an ankle joint linking the shin section and foot section, wherein the knee joint includes a knee flexion control device and the ankle joint includes an ankle flexion control device, the prosthesis further comprising a plurality of sensors arranged to generate sensor signals indicative of at least one respective kinetic or kinematic parameter of locomotion, or of walking environment, the prosthesis further comprising an electronic control system coupled to the said sensors to receive the sensor signals and to the flexion control devices to feed control signals to the said control devices in order dynamically and automatically to modify the flexion control settings of the knee joint and the ankle joint in response to the sensor signals, and wherein, the sensors include a sensor associated with the shin section which is arranged, in combination with the electronic control system, to generate signals representative of a shin section bending moment, and to feed control signals to the ankle flexion control device in response to the signals representative of the shin section bending moment. Preferably, the ankle damping resistance is varied in response to the sensed bending moment and, more preferably, the knee damping resistance as well.

According to a third aspect of the invention, there is provided a lower limb prosthesis comprising an attachment section, a shin section, a foot section, a knee joint pivotally connecting the attachment section and the shin section, and an ankle joint pivotally connecting the shin section and the foot section, the knee joint including a dynamically adjustable knee flexion control device for damping knee flexion, wherein the prosthesis further comprises an inclination sensor associated with the ankle joint or foot section and operable to generate inclination sensor signals indicative of ground inclination, and an electronic control system coupled to the inclination sensor and to the knee flexion control device, the arrangement of the sensor, the electronic control system and the knee flexion control device being such that the damping resistance of the knee flexion control device is variable in response to the inclination sensor signals. The damping resistance at the knee may be controlled in part, also, by the values produced by the electronic control system for ankle joint damping resistance. In a particular embodiment of the invention, the control system is arranged such that when the inclination sensor signals indicate descent, the stance phase resistance to flexion, in this case to bending of knee, is decreased during the stance phase. Thus, whereas during an initial part of the stance phase, the resistance to flexion is high such that the knee may be nearly locked in order to provide stability during stance, in a subsequent part of the stance phase the resistance is decreased to allow greater yielding under the load imposed by the amputee's weight in order to prepare for the swing phase. The reduction in resistance may be stepped or progressive.

According to a fourth aspect of the invention, there is provided a lower limb prosthesis comprising an attachment section, a shin section, a foot section, a knee joint linking the attachment section and the shin section, and an ankle joint linking the shin section and foot section, wherein the knee joint includes a knee flexion control device and the ankle joint includes an ankle flexion control device, the prosthesis further comprising a sensor associated with the knee joint which is coupled to the electronic control system and is arranged, in combination with the electronic control system, to generate signals indicative of a speed of locomotion, wherein the ankle flexion control device is a device capable of variably damping ankle joint flexion and arranged in combination with electronic control system to alter the resistance to ankle flexion damping in response to the signals indicative of speed of locomotion.

According to a fifth aspect of the invention, there is provided a lower limb prosthesis comprising an attachment section, a shin section, a foot section, a knee joint pivotally connecting the attachment section and the shin section, and an ankle joint pivotally connecting the shin section and the foot section, the knee joint including a dynamically adjustable knee flexion control device for damping knee flexion, wherein the prosthesis further comprises a plurality of sensors each arranged to generate sensor signals indicative of at least one respective kinetic or kinematic parameter of locomotion or of walking environment, and an electronic control system coupled to the sensors and to the knee flexion control device in order dynamically and automatically to modify the flexion control setting of the knee joint in response to signals from the sensors, including from one of the said sensors which is operable to generate inclination sensor signals indicative of ground inclination, and wherein the arrangement of the sensors, the electronic control system and the knee flexion control device is such that when the inclination sensor signals indicate descent of a downward incline, the damping resistance of the knee flexion control device is set to a first level during a major part of the stance phase of the gait cycle and to a second, lower level during a major part of the swing phase of the gait cycle, and wherein, during an interval including a latter part of the stance phase, the knee flexion control device is adjusted so that the damping resistance to knee flexion is between the first and second levels.

In contrast, in the preferred embodiment, the arrangement is such that in a level walking mode or ramp-up mode, the damping resistance of the knee flexion control device is switched substantially directly from the first level or one similar thereto to the second level or one similar thereto. In other words, switching of the knee flexion damping resistance to the second level is delayed in the ramp-down mode, as compared to the switching in the level walking mode, by virtue of an adjustment of the knee flexion control device to one or more intermediate resistance levels. This allows to give some additional support at the end of stance phase while not preventing the initiation of swing phase in a controlled manner.

It is preferred that signals fed to the knee flexion control device cause the flexion resistance to be reduced in a step change at the start of the said interval to a third, predetermined intermediate level between the first level and the second level, and to be reduced in a further step change at the end of the said interval to the second level. Alternatively, the signals fed to the knee flexion control device during the said interval cause the knee flexion damping resistance to be progressively reduced from the first level to the second level.

Typically, the duration of the said interval is at least 10 percent of the duration of the stance phase (the stance phase ending at toe-off, i.e. the point at which the foot section leaves the ground). More preferably, the interval is at least 15 percent of the stance phase duration and may be in excess of 20 percent. It is also preferred that the interval spans the toe-off point, beginning at or shortly after a shin bending moment maximum and ending as the knee flexion angle is increasing during the swing phase of the gait cycle. In the preferred embodiment, the interval ends when the knee flexion angle has increased to a predetermined threshold at between 30 percent and 70 percent of the maximum knee flexion angle achieved in the swing phase.

In the ramp down mode, the electronic control system preferably follows a ramp down resistance program controlling switching of the knee flexion control device from the first level to the third level and from the third level to the second level. Switching of the knee flexion damping resistance from the first level to the third level may be performed in response to a measured kinetic parameter, e.g. a moment or force, preferably the shin bending moment. Switching of the knee flexion damping resistance to the second level at the end of the interval is preferably performed in response to a measured kinematic parameter, e.g. a relative linear or angular displacement of one limb segment with respect to another, or related derivatives, e.g. velocities or accelerations. In the preferred embodiment, the kinematic parameter is the measured knee angle or an equivalent thereof.

The invention will now be described by way of example with reference to the drawings, in which:—

FIGS. 4A to 4D are representations of a multiple-layer matrix group defining relationships between input conditions derived, e.g., from sensed kinetic and kinematic parameters of locomotion, and outputs for flexion control devices forming part of the prosthesis of FIG. 1, FIG. 4A showing a main matrix and FIGS. 4B, 4C and 4D showing lower-level matrices for, respectively, walking up a ramp, walking down a ramp, and walking at different speeds on a level surface;

FIGS. 5A to 5D are graphs illustrating the variation of selected parameters over the course of the walking gait cycle; and FIG. 6 is a composite graph illustrating the variation of knee flexion damping resistance in a ramp down mode.

Figure 1A:
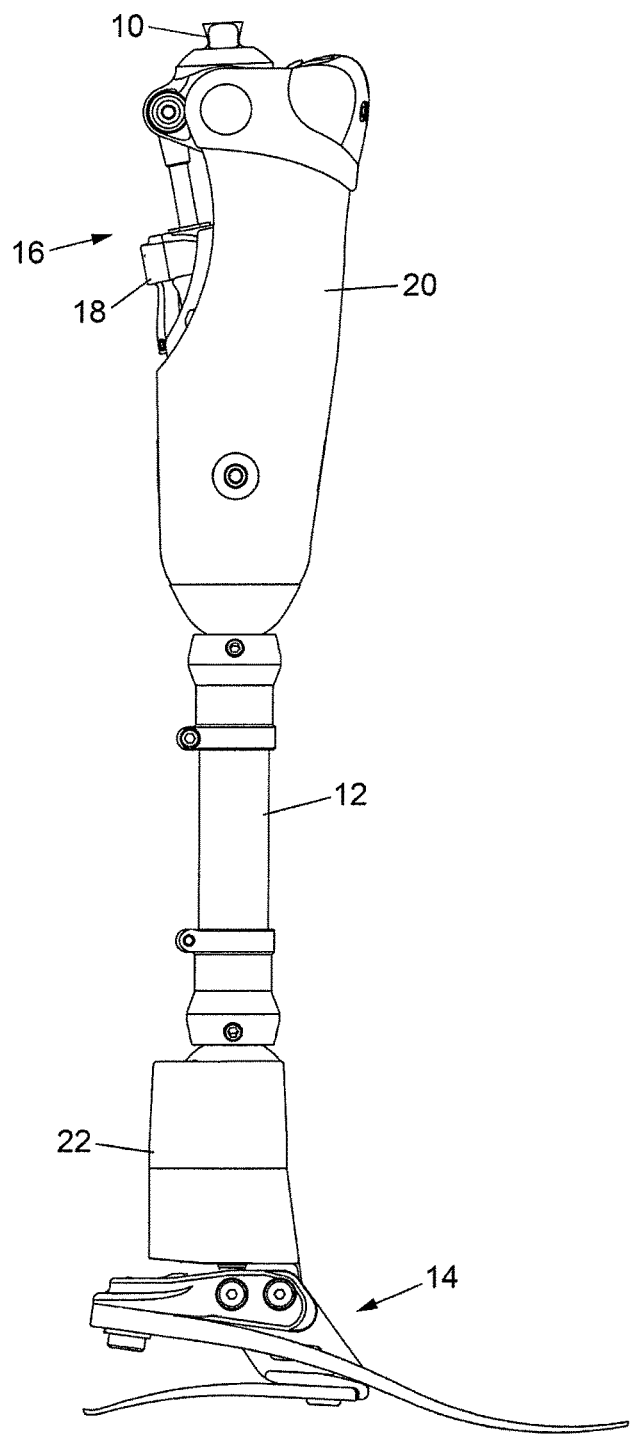
FIG. 1A is a side elevation of a lower limb prosthesis in accordance with the invention.

Referring to FIG. 1A, a lower limb prosthesis in accordance with the invention has an attachment section 10 for attaching the prosthesis to, for instance, a stump socket (not shown), a shin section 12 and a foot section 14. The shin section 12 is linked to the attachment section 10 by a knee joint 16 which, in this case, is a uniaxial knee joint incorporating a flexion control device 18 housed in a knee cradle 20 to which the shin section 12 is attached. Linking the foot section 14 to the shin section 12 is an ankle joint 22 incorporating an ankle flexion control device which will be described hereinafter.

Figure 1B:
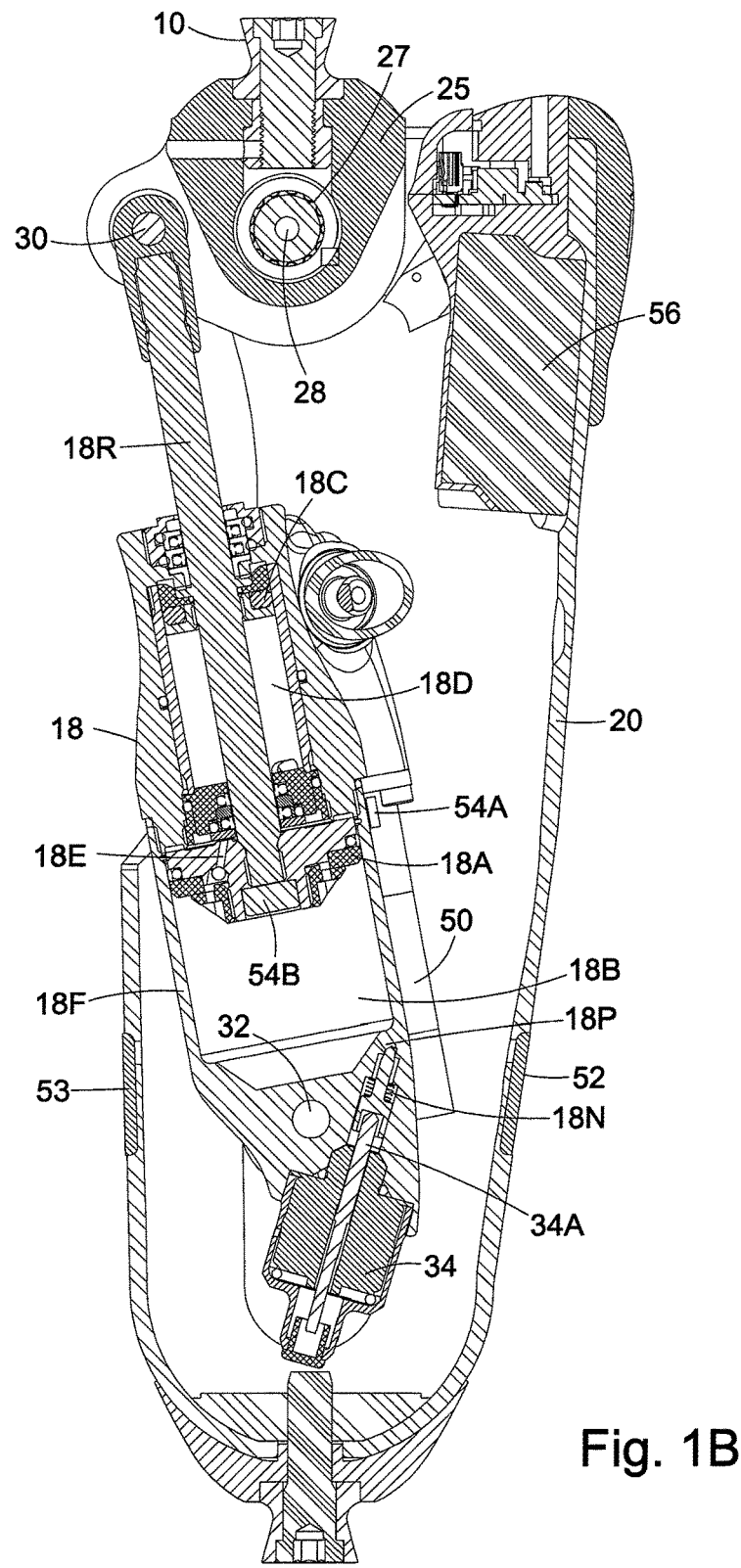
FIG. 1B is a longitudinal cross-section of a knee joint of the prosthesis of FIG. 1A.
Figure 1C:
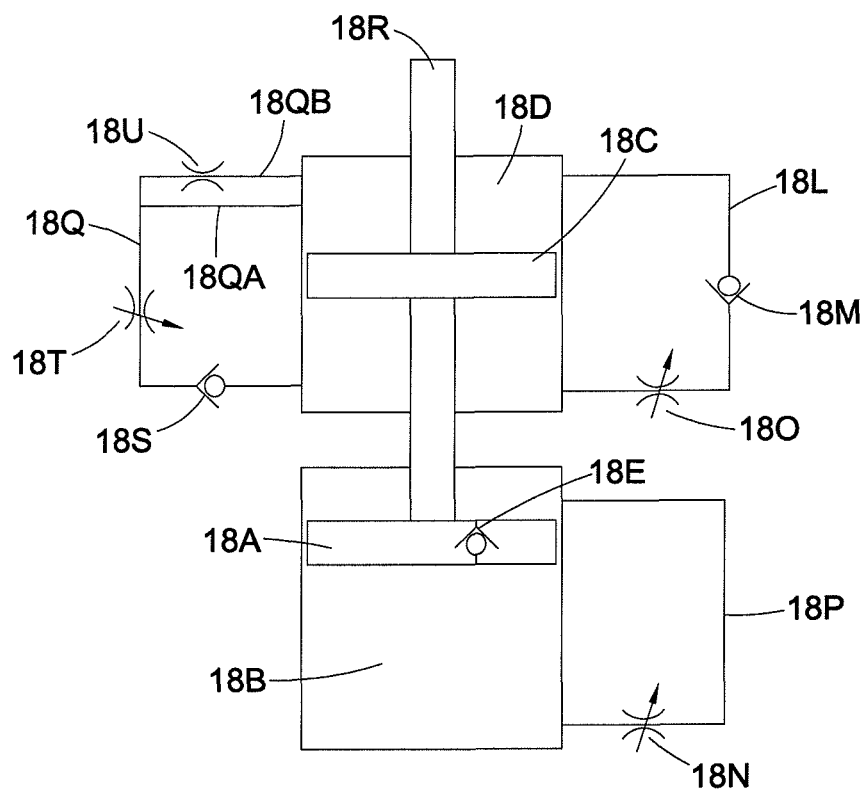
FIG. 1C is a schematic representation of hydraulic and pneumatic circuits in a knee flexion control device in the knee joint of FIG. 1B.

The knee joint 16 is shown in more detail in FIG. 1B. Referring to FIG. 1B, the knee joint has a knee chassis 25 to which the attachment section 10 is rigidly mounted and carries a pivot 27 defining a knee axis 28. The shin cradle 20 is attached to the knee chassis 25 by the pivot 27 so that, when the knee joint is flexed, the shin cradle 20 pivots relative to the attachment section 10 about the knee axis 28.

Pivotally coupled to a posterior part of the knee chassis 25 and to a lower part of the shin cradle 20 by upper and lower control device pivots 30, 32, the knee flexion control device 18 is in the form of a hybrid pneumatic and hydraulic piston and cylinder assembly for controlling both flexion and extension of the knee joint. Being a hybrid control device, it comprises a housing having two cylinders and two pistons, the latter both being mounted on a common piston rod 18R. Referring to FIG. 1B in conjunction with FIG. 1C, a first piston 18A, hereinafter referred to as the "pneumatic piston" is reciprocable in a first pneumatic piston chamber 18B, and a second piston 18C, hereinafter referred to as the "hydraulic piston" is reciprocable in a second, hydraulic chamber 18D. The arrangement and function of the pneumatic piston 18A and associated parts of the flexion control device are generally similar to those of the piston and cylinder assembly disclosed in published British Patent Application GB2280609A. The pneumatic piston 18A contains a bypass passage 18E including a non-return valve which is oriented such that the pneumatic piston 18A resists movement of the piston rod 18R much more during flexion of the knee joint than during extension. Indeed, in this region, resistance to extension is negligible. Resistance of the pneumatic part of the control device 18 to flexion at the knee joint is controlled by a needle valve 18N which is adjustable by a first electrical stepper motor 34 and an associated screw-threaded shaft 34A connected to the needle member of the needle valve. The needle valve 18N lies in a passage 18P in a lower housing part 18F of the control device 18, the passage interconnecting the upper and lower parts of the pneumatic chamber 18B on opposite respective sides of the pneumatic piston 18A, and emerging to the outside at a port (not shown) at the top of the pneumatic chamber 18B. Operation of the motor 34 causes the shaft 34A to move axially so that the needle member moves into or out of a passageway forming part of the passage 18P to vary the orifice area.

The passage 18P constitutes a second bypass passage interconnecting the chamber spaces on opposite sides of the pneumatic piston 18A. It will be understood, then, that the flexion resistance provided by differential pressure across the piston 18A depends largely on the restriction created by the setting of the needle valve 18N by the motor 34.

A first hydraulic bypass passage 18L contains a non-return valve 18M oriented so as to close the passage during knee extension movements. The passage 18L also contains an adjustable rotary valve 18O connected via a gear mechanism to a second electric motor 50 mounted on the side of the housing 18F of the knee flexion control device 18. Variable valve 18O has a through-passage which communicates with the bore of the bypass passage 18L to a varying degree depending on the angular position of the valve 18O, the cross-section of the passage being shaped to provide a progressive change in orifice area as the rotatable part of the valve is driven by the motor 50.

Owing to the orientation of the non-return valve 18M, the first hydraulic bypass passage 18L and its associated adjustable valve 18O control the level of knee flexion resistance due to the hydraulic part of the control device 18 according to the electrical signals controlling the motor 50.

A second hydraulic bypass passage 18Q in the hydraulic part of the control device 18 has a non-return valve 18S which is oppositely oriented to that of the first bypass passage 18L such that a second rotary valve 18T, which restricts the flow of hydraulic fluid through passage 18Q, controls the resistance to knee extension when activated. In this embodiment of the invention, the second rotary valve 18T is manually presettable.

The second hydraulic bypass passage 18NQ is branched into two passages 18QA, 18QB which are ported into the hydraulic chamber 18D at different locations so that one of the branches 18QA is covered by the piston 18C as the knee joint nears full extension. The other branch 18QB remains uncovered substantially to full extension. This second branch 18QB has a restriction 18U, whereas the first branch 18QA is open, so that as the piston 18C nears the full extension position, the restriction 18U takes effect over a final portion of the piston stroke, as the piston itself restricts fluid flow through passage 18QB, to provide progressive terminal impact damping. The base resistance to extension is determined by the setting of the manually adjustable second rotary valve 18T.

Activation of the hydraulic valve 18O is controlled by an electronic control system, as described below, in order that, at least during the stance phase of the walking gait cycle, the knee flexion control device provides predominantly hydraulically controlled flexion and extension, whereas during the swing phase, the control is predominantly pneumatic.

As part of the electronic control system, the shin cradle 20 carries two strain gauges 52, 53, one mounted on an anterior wall of the cradle 20 and the other on an opposite posterior wall. These sensors are used for measuring the shin bending moment when the prosthesis is loaded. The knee joint also carries a knee angle sensor in the form of a magnetoresistive transducer 54A mounted on the side of the knee control device housing 18F and a magnet 54B on the piston 18A.

In the upper anterior part of the shin cradle, space is provided for a battery 56 for powering the electronic control system.

Figure 1D:
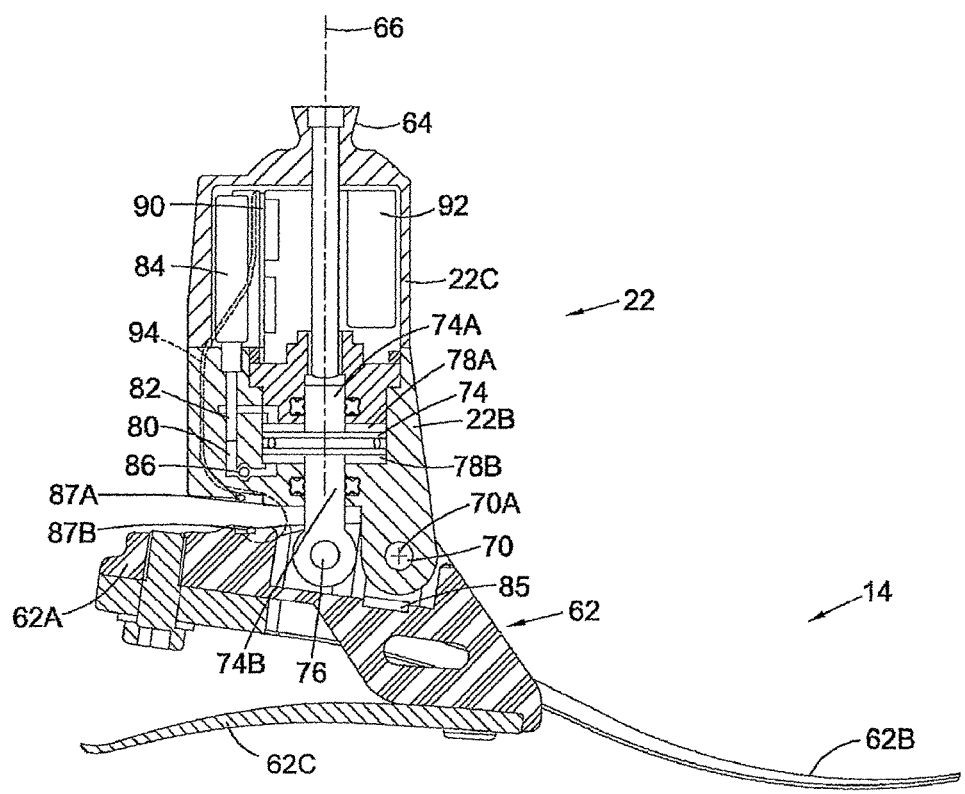
FIG. 1D is a longitudinal cross-section of a foot/ankle assembly of the prosthesis of FIG. 1A.

Referring now to FIG. 1D, the preferred prosthesis has a foot keel 62 comprising a rigid carrier 62A. Independently coupled to the rigid carrier 62A are a toe spring 62B and a heel spring 62C. The keel 62 is largely formed from carbon fibre composite material and can be surrounded by a foam cosmetic covering (not shown).

Coupled to the foot keel 62 is the ankle joint 22 which is substantially cylindrical in shape and coaxial with the shin section 12 (see FIG. 1A), the ankle joint carrying an upper alignment interface 64 in the form of a pyramid-shaped shin connection interface 64 which defines a longitudinal shin connection axis 66. The ankle joint 22 connects the shin section 12 to the foot keel 62A of the foot 60, the mounting to the foot keel 62A being by way of an ankle flexion pivot 70 defining an ankle flexion axis 70A.

The ankle joint 22 has an ankle joint body 22B which forms the cylinder of an ankle joint piston and cylinder assembly having a piston 74 with upper and lower piston rods 74A, 74B, the lower piston rod being pivotally connected to the foot keel 62A at a second pivotal connection 76, this second pivotal connection defining a second medial-lateral axis which is spaced, in this case, posteriorly from the flexion axis 70A. It will be seen that, as the ankle joint body 22B pivots about the flexion axis 70A, the piston 74 moves substantially linearly in the cylinder formed by the body.

The cylinder is divided into upper and lower chambers 78A, 78B. These chambers are linked by two bypass passages 80 in the ankle joint body 22B, one of which is visible in FIG. 1D. The other passage does not appear in FIG. 1D since it is located in front of the sectional plane. However, its configuration is almost identical. These two bypass passages 80 each communicate with both the upper chamber 78A and the lower chamber 78B of the cylinder via two valves. Each contains a respective damping resistance control valve 82 which has an associated actuator in the form of a servo motor 84. Operation of the servo motor 84 rotates a valve member of the valve 82 progressively to increase or decrease the orifice area of the valve 82. Each bypass passage 80 also contains a respective non-return valve 86. This adjustable-area orifice valve 82 and the non-return valve 86 are arranged in series in the bypass passage 80, between the upper and lower cylinder chambers 78A, 78B.

The bypass passage 80 appearing in FIG. 1D has its non-return valve 86 oriented to allow the flow of hydraulic fluid from the lower chamber 78B to the upper chamber 78A. The other bypass passage (not shown) has its non-return valve oriented in the opposite direction. Accordingly, one of the passages 80 is operative during dorsi-flexion and the other during plantar-flexion. Continuous yielding movement of the foot component 14 relative to the ankle joint body 22B about the flexion axis 70A is possible between dorsi-flexion and plantar-flexion limits defined by the abutment of the piston 74 with, respectively, the lower wall and the upper wall of the cylinder containing the piston 74. The level of damping for dorsi-flexion and plantar-flexion is independently and automatically presettable by the respective adjustable-area orifices by means of the electronic control system described below.

The electronic control system has a sensor 85 in the form of an accelerometer mounted on the foot keel 62A and a two-part ankle flexion angle sensor 87A, 87B, the two parts being mounted in registry with each other on the ankle joint body 22B and the foot keel 62A. The ankle joint casing 22C not only houses the two servo motors 84 for the adjustable damping resistance control valves 82; they also provide space for a processor board 90 and a second battery 92. Wires 94 link the ankle flexion angle sensor 87A, 87B to the processor board 90. Other wires (not shown) link the other sensors, the batteries, and the motors of the knee joint to the processor board 90.

Figure 2:
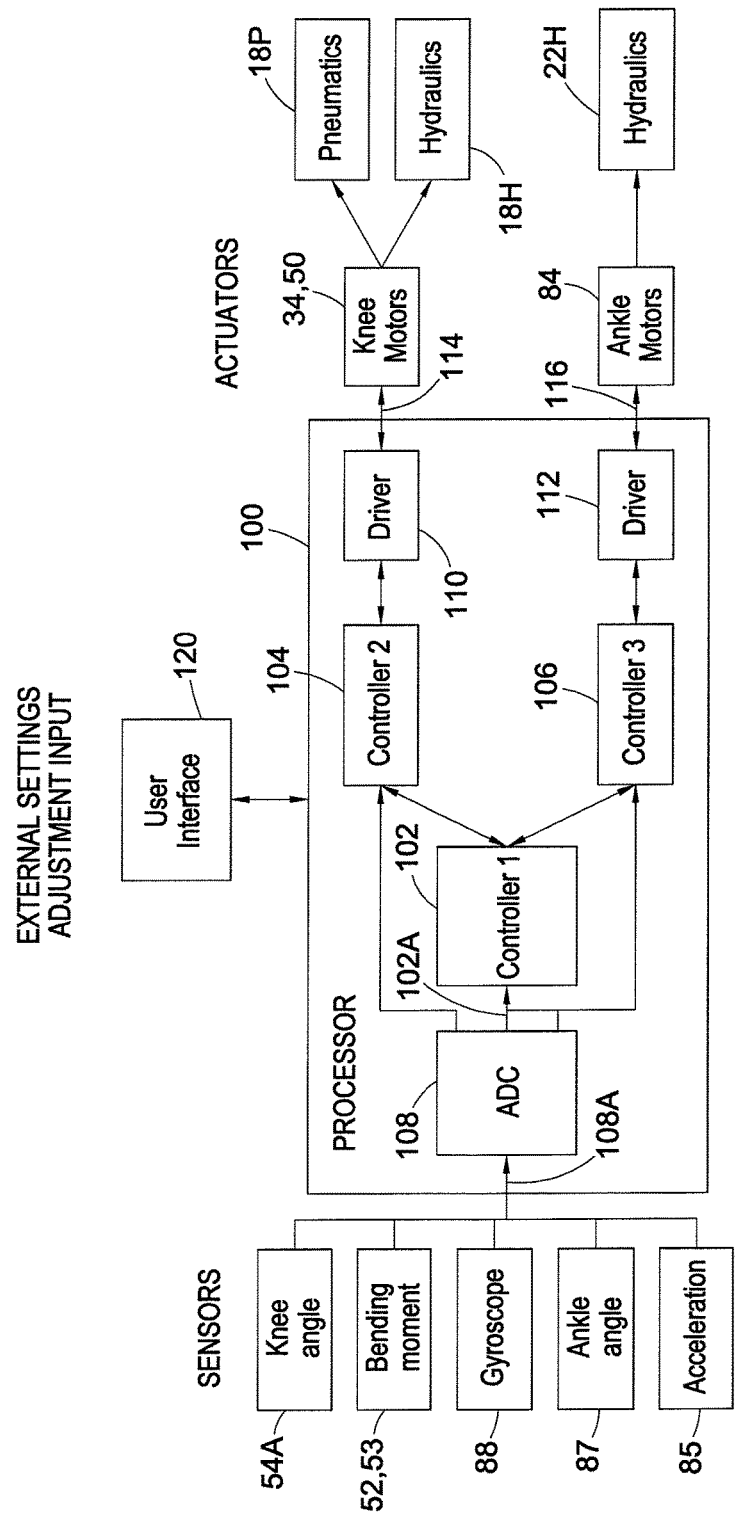
FIG. 2 is a block diagram of an electronic control system, together with sensors, for the prosthesis of FIG. 1.

Referring, now, to FIG. 2, the preferred electronic control system comprises a processor section 100 with three 8-bit microprocessor controllers. (16-bit controllers may be used as an alternative.) The controllers comprise a main controller 102 coupled to two slave controllers, these being a knee controller 104 and an ankle controller 106. Coupled to an input port 102A of the main controller 102 is an analogue to digital converter 108 with a plurality of inputs shown as an input port 108A in FIG. 2. These comprise analogue inputs for receiving sensor signals from the above-described sensors located in different parts of the prosthesis. Accordingly, the data received by the controller 102 is representative of a number of kinetic and kinematic parameters associated with use of the limb in different activity modes. The activity modes, such as level walking, walking on an incline, standing, sitting down, etc. are detected on the basis of such parameters by the main controller 102, as described below, in accordance with preset rules.

According to further rules stored in the main controller 102, instructions are fed therefrom to the knee controller 104 and the ankle controller 106 which generate control signals for knee and ankle motor drivers 110, 112. The motors 34, 50 associated with the knee joint, as described above with reference to FIG. 1B, exchange signals with the processor section 100 via connections 114 with the first of the drivers 110, including driver signals for driving the knee motors to required positions which are verified by feedback signals via the connections 114. As described above, the knee motors 34, 50 set the valves controlling the movement of the pneumatic piston and the hydraulic piston in the respective parts 18P, 18L of the knee control device 18 (see FIG. 1B).

Similarly, the ankle motors 84 (described above with reference to FIG. 1D) exchange signals with the processor section 100 via connections 116 to the second driver 112, the signals comprising driving signals and feedback signals in order that the ankle motors 84 set the valves controlling the movement of the hydraulic piston in the ankle joint control device 22H contained in the ankle joint 22, as described above with reference to FIG. 1D.

A user interface 120, coupled to the processor section 100, comprises a wireless communication section for exchanging wireless signals with a PC or tablet computing device. Programming can also be done by a defined HMI (operator interface) using, e.g. two buttons, an LED, and a beeper, indicating the status of programming.

The control system uses open architecture, both in hardware and software terms to allow parts to be added or to accommodate, for instance, alternative or additional input and output signals, e.g. for signals from another electronic control system in, e.g. a second lower limb prosthesis in the case of a bilateral amputee. This open architecture provides a technology platform with plug-in modules that can be changed according to requirements. For instance, in the case of a bi-lateral amputee information about the second limb is provided. Sensor data from other sensors may be provided. However, the bilateral option shall not only include communication possibilities for a double transfemoral (above-knee) amputee, for example, but also communication between a transfemoral prosthesis and a transtibial (below-knee) prosthesis which means, in effect, communication between a processor-controlled foot/ankle joint is possible as this is beneficial for the overall gait performance and coordination. Overall sharing of information between different joints and/or components in various combinations and configurations is possible owing to the open-architecture approach.

The main controller 102 is programmed to derive from the digital representations of the sensor signals kinetic or kinematic parameters of locomotion thereby to measure gait characteristics such as velocity including information about the relevant parameters step rate and stride length, and gait phase, and the step-to-step variability in such characteristics, thereby to produce control signals from the knee and ankle controllers 104, 106 to modify the settings of the knee and ankle joint control devices so as to optimise the gait of the amputee.

Included in the programming of the main controller 102 is a self-calibrating routine, as described in the above-mentioned EP1334891 and WO2007/110585, for convenient and straightforward modification of the control characteristics for the individual amputee. Velocity, i.e. the speed of locomotion, in particular walking speed or gait cycle frequency, and gait phase are preferably computed from the outputs of the knee angle sensor 54A and the bending moment strain gauges 52, 53, although in some circumstances, these parameters may be derived from the outputs of a gyroscope 88 mounted, e.g. on the shin section and the accelerometer 85 mounted at the foot level. Changes in the walking surface and the velocity of the foot in the global reference frame (kinematic changes) are preferably measured using the signals from the accelerometer 85 and the ankle angle sensor 87 to drive modification of the settings of the control device of the ankle joint 22 (FIG. 1D), as described in the above-mentioned WO2008/103917.

The main controller 102, collecting data derived from the outputs of sensors associated with both the knee joint and the ankle joint, i.e. from different regions of the prosthesis, allows improved control of the knee joint and ankle joint control devices and advanced analysis of gait and mode based on a combined representation of data relating to different regions of the prosthesis. The main controller 102 sends direct commands and additional gait-related information to the knee controller 104 and the ankle controller 106 which act, effectively, as slave controllers in a hierarchical, distributed control system. The knee controller 104 and the ankle controller 106 do, however, have some autonomy for safety should, for instance, no valid signals be forthcoming from the main controller 102.

The main controller 102 has a non-volatile memory for storing values of a limb control matrix relating input conditions derived from the sensor signals and output data which is used by the main controller and the slave controllers 104, 106 to determine the control signals for the flexion control devices 18A, 18C, 74. Matrix values can be downloaded for external storage and communication via the user interface 120 as well as being reloaded from external devices. Alternatively, control matrix values may be stored locally in the non-volatile memory of the slave controllers 104, 106, the main controller 102 having access to these values and the ability to change them.

Figure 3A:
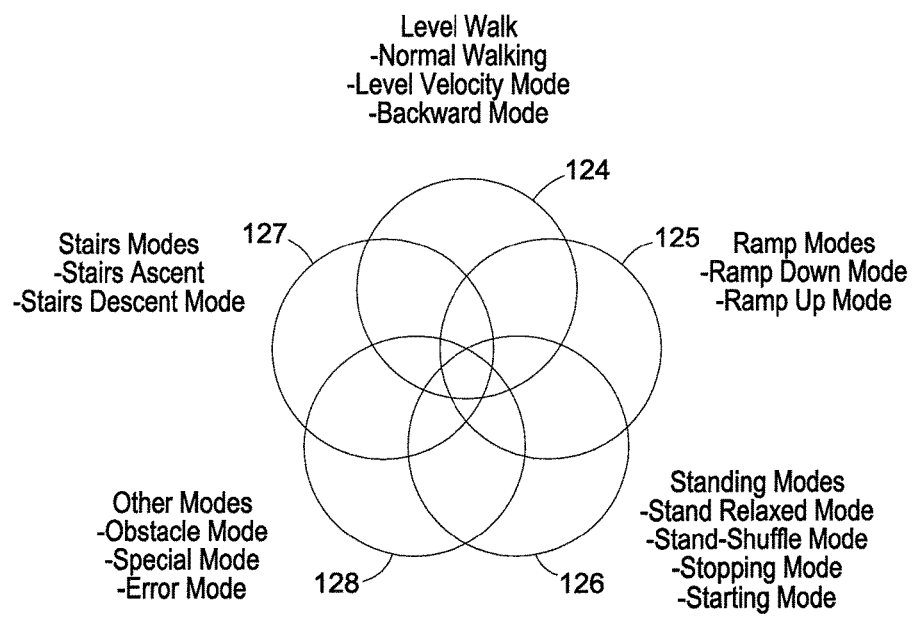
FIG. 3A is a Venn diagram indicating different activity modes defined within the electronic control system, and their interrelationships.

The processor section 100 operates on a finite-state control basis. Referring to FIG. 3A, the status of the main controller 102 (FIG. 2) is defined according to a series of activity modes. These activity modes are grouped as modes 124 associated with level walking, ramp modes 125, standing modes 126, stairs modes 127, and other modes 128, such as an obstacle mode, a special mode, and an error mode. The intersections of the Venn diagram areas are indicative of the transitions which may be made from one mode to another. Other transitions such as going from ramp down to ramp up directly are also possible. The preferred finite-state control possibilities are shown more clearly in FIG. 3B. In this case, the modes include a Normal Walking mode 130, a Ramp Up mode 132, a Ramp Down mode 134, and so on, as shown in the diagram. The list of modes in the diagram is not exhaustive. The Normal Walking mode is configures as the central point of the diagram. As shown by the interconnections between the different modes, the main controller switches or transitions from one mode to another, according to sensor inputs received as sensor data from the analogue to digital converter (ADC) 108 (FIG. 2). The rules programmed into the main controller 102 then determine how the knee motors 34, 50 and ankle motors 84 (FIG. 2) are driven in response to the change of mode and in response to other changes in the data obtained from the sensors.

Figure 3B:
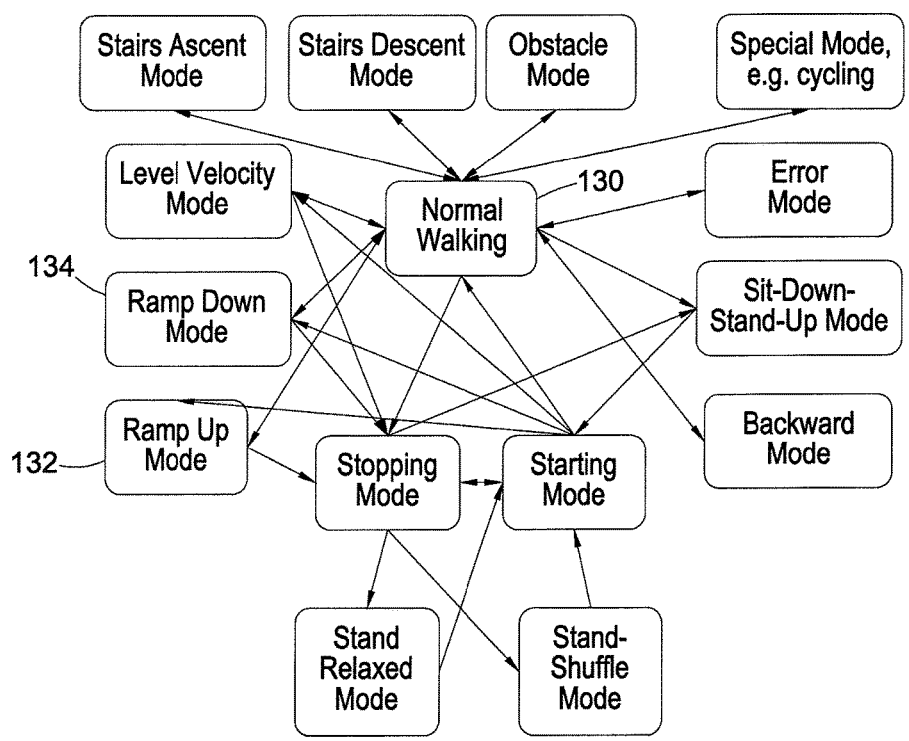
FIG. 3B is a finite state diagram indicating the different activity modes defined within the electronic control system, and transitions between the modes.
Figure 3C:
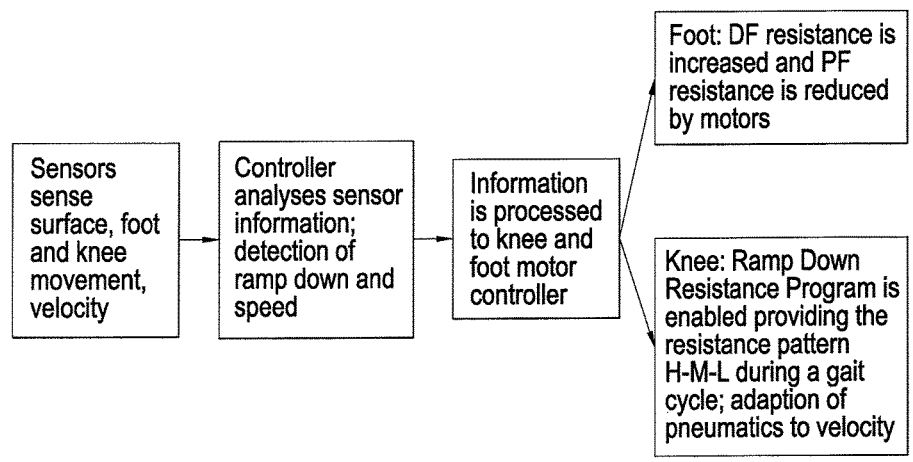
FIG. 3C is a flow chart illustrating a typical set of operations performed by the electronic control system and flexion control devices of the prosthesis.

Thus, for instance, as shown in FIG. 3C, the commencement of walking down an incline after a period of walking on the level may be detected and responded to by the following steps:

The foot sensors (the accelerometer 85 and the ankle flexion angle sensor 87 (FIGS. 1D, 2)) generate sensor signals indicative of a change in ground inclination (step 140).

The main controller 102 and/or the ankle controller 106 analyze the digitized versions of the sensor signals and determine that the surface has changed to a downwardly inclined ramp (step 142).

Based on a stored matrix of relationships between, on the one hand, activity mode and kinetic or kinematic parameter values and, on the other hand, respective flexion control resistances, the change in mode is translated into new settings for the knee and ankle motors (step 144).

Via the motor drivers 110, 112, the knee motors 34, 50 and ankle motors 84 (FIG. 2) are driven to the new respective settings which, in this case, involves driving the servomotor 50 to a new setting in which the hydraulic part of the knee joint control device 18 is set to provide intermediate yield in the Ramp Down mode and the pneumatic part of the control device 18 is driven to different settings according to walking speed, in the same way as in the level walking (normal walking) mode (step 146). Concurrently, the ankle motor settings are changed to increase the dorsi-flexion resistance provided by the ankle joint control device and to reduce the plantar-flexion resistance (step 148).

Similar basic sequences apply to the other mode transitions shown in FIG. 3B, the sensors used and the actions performed being governed according to the sensed modes. In this embodiment, the settings to which the actuators are driven are governed by a 6×5 main matrix, as shown in FIG. 4A, and three N×5 lower level matrices, as shown in FIGS. 4B, 4C and 4D. The matrix rows correspond to different activity modes (listed in the left-hand column in each case), and the matrix columns indicate the settings of the four above-described flexion resistance control device parts, those of the hydraulic part of the knee control device being indicated for the swing and stance phases separately The five primary resistance settings are adapted according to the individual amputee. The normal settings for the ankle joint (foot) plantar-flexion and dorsi-flexion resistances in the FIG. 4A matrix are moderate resistance settings for normal, medium-speed Level Walking as shown in FIG. 4D. The normal setting of the knee joint is that shown in a "Level Velocity" mode in FIG. 4A and is characterised by high hydraulic resistance during stance and low hydraulic resistance during swing, and variation of pneumatic flexion resistance according to walking speed.

In practice, the matrix for each mode or event is composed of five primary values, as shown in the columns of the tables of FIGS. 4A to 4D. In several instances, bands of values are pre-programmed to provide a range of values from which a particular value is selected in each case to suit the amputee.

The main modes are those appearing in the left-hand column of FIG. 4A, i.e. Ramp Up, Ramp Down, Level Velocity (Level Walk), Stairs Down, Stand Relaxed, and Sitting. In FIG. 4A, the asterisk (*) indicates the existence of sub-modes, these appearing in FIGS. 4B, 4C and 4D respectively. The values in the body of each matrix represent the level to which flexion (or extension) of the respective joint is resisted. Thus, "VL" means very low resistance, "L" means low resistance, "M" means medium resistance, "H" means high resistance, and "VH" means very high resistance. "M/H" means a resistance level between medium and high resistance, while "H−" is resistance which is a little bit less than high resistance, and "H+" means resistance a little higher than a high resistance. "VL−", "L−", "L+" and "VH+" are to be correspondingly interpreted.

With regard to the knee hydraulic settings, the dollar sign $ at the head of the respective columns means that when the knee control device resistance value is not indicated explicitly (i.e. by a single value) the resistance is switched between two levels, (a) between typically H or H− and M or (b) as the toe is loaded to select the lower value, and as the limb is extended to select the higher value. With regard to the setting of the pneumatic part of the knee control device, the hash sign # at the head of the column indicates that when the resistance value is not explicitly indicated, the pneumatic part of the control device adapts automatically to the speed of walking, regardless of the surface or other conditions.

Accordingly, in the "Level Velocity" mode, for level walking, the resistance due to the pneumatic part of the knee control device varies from low to high according to walking speed, as shown in FIG. 4D. Indeed, the pneumatic resistance may increase to VH for very fast level walking. Resistance to plantar-flexion and dorsi-flexion at the ankle during the velocity/level walking mode, as indicated in FIG. 4D, according to speed.

Referring back to the main matrix of FIG. 4A, it will be seen that the resistance values for Ramp Up and Ramp Down differ in certain respects to those for the Velocity/Level Walk mode. Thus, for instance, the resistance to plantar-flexion at the ankle is lower, generally, when descending a ramp than during level walking, and higher when ascending a ramp. Dorsi-flexion resistance at the ankle tends to be higher when descending a ramp and lower when ascending. However, at the same time, these values vary according to speed/velocity and according to the steepness of the ramp, and during transitions between modes, as indicated in the sub-matrices of FIGS. 4B and 4C.

Referring to FIG. 4C, in both the stance and swing phases of the Ramp Down mode, an intermediate hydraulic resistance level (M) is indicated. This level is set by the knee flexion control device to occur during an interval comprising a latter part of the stance phase and an initial part of the swing phase. Thus, during each gait cycle in the Ramp Down mode, the transition from stance to swing is characterised by a stepwise reduction from the high (H or H−) level to the low (L) level, the interval during which the intermediate (M) level applies spanning the toe-off point at the end of the stance phase. This increased yielding of the knee joint towards the end of the stance phase aids descent. The main benefit in the ramp down mode is that the change between the flexion resistances between high and low (which is the normal profile in other modes) is reduced (high to intermediate and then to low during the end part of the stance phase). This creates, firstly, some extra support as the amputee has some added resistance at the end of stance. Able-bodied people then tend to use their muscles to brake slowly going down a ramp so that they don't accelerate or only accelerate in a controlled matter. The amputee doesn't have this ability with the prosthetic limb. Secondly, the foot and ankle already brake going down a ramp but the additional resistance at the knee at end of the stance phase gives the amputee a feeling of extra security and grip and has the potential beneficially to decelerate the amputee.

It should be noted that no reduction of flexion damping resistance occurs at the knee during descent of a steep ramp, as shown by the Steep Ramp sub-modes in FIG. 4C. In this sub-mode, there is little or no loading of the toe because the amputee uses knee yield to descend the steep ramp.

Figure 3D:
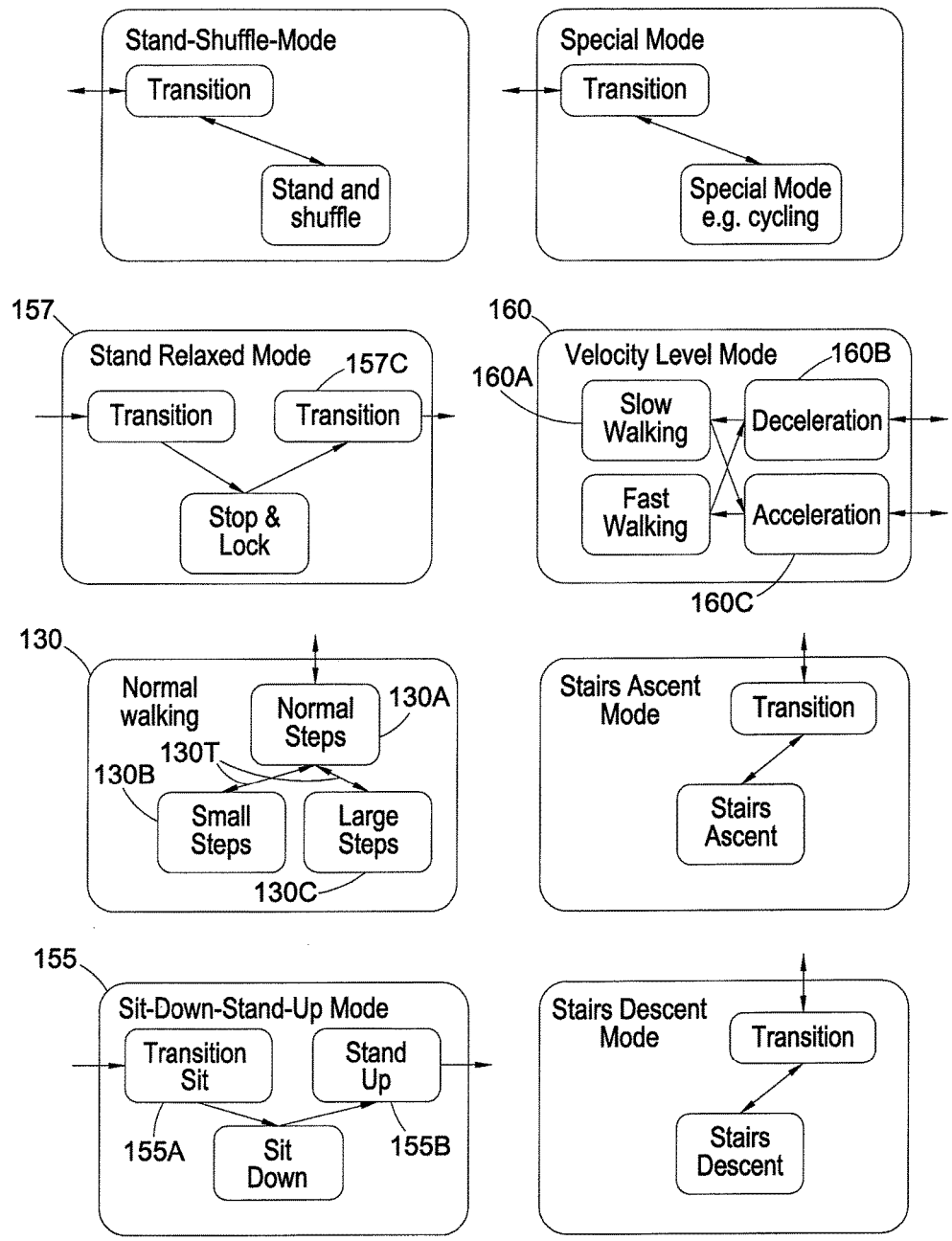
FIG. 3D is a first series of more detailed finite state diagrams used by the electronic control system.
Figure 3E:
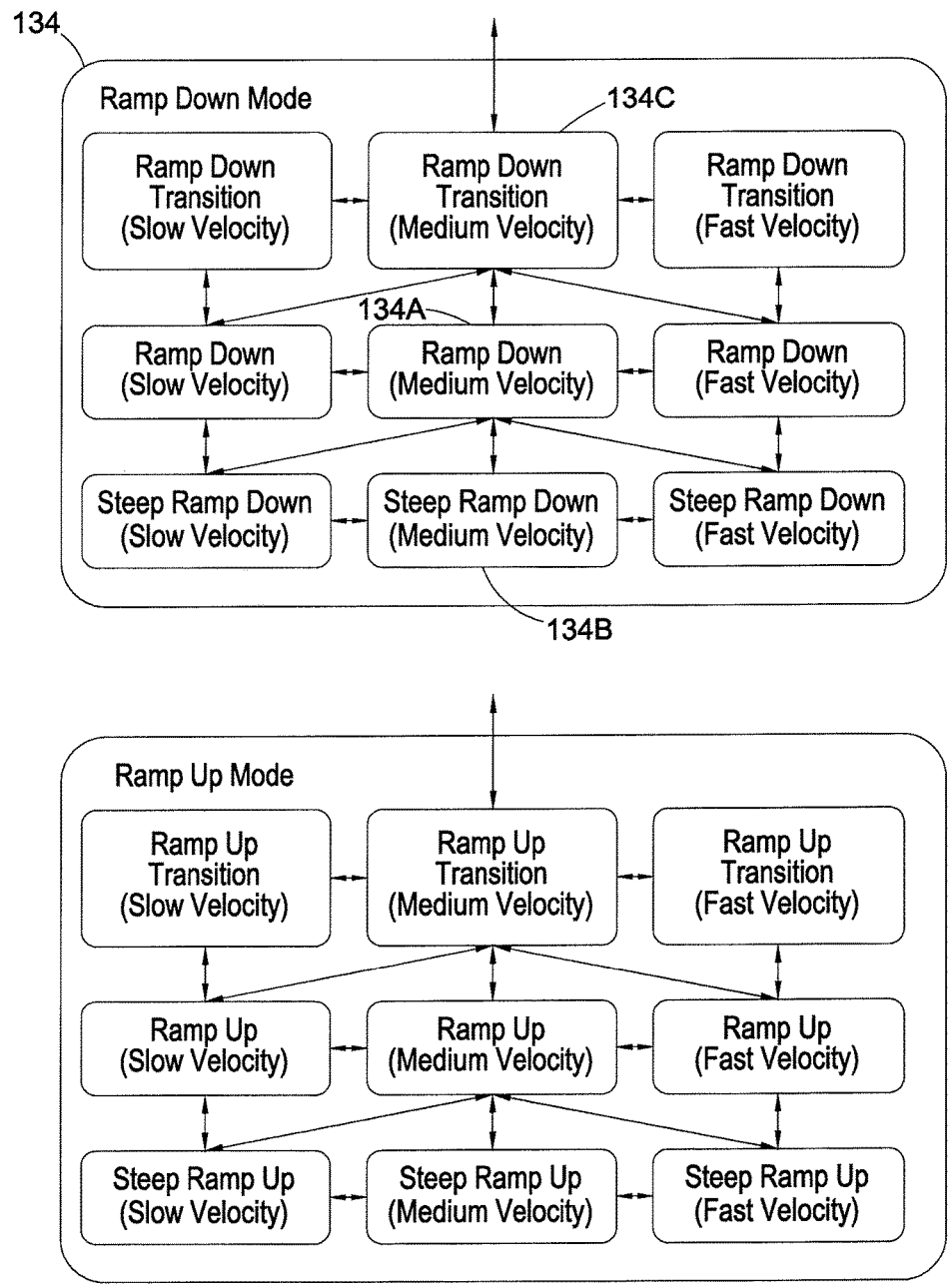
FIG. 3E is a second series of more detailed finite state diagrams used by the electronic control system.

Each basic mode described above with reference to FIGS. 3A and 3B and FIGS. 4A to 4D has associated transition states, as indicated by the more detailed finite state diagram of FIGS. 3D and 3E. In addition, in this embodiment, the basic modes are divided into further sub-modes. To give examples from FIGS. 3D and 3E, therefore, the normal walking mode 130 has three such sub-modes: Normal Steps 130A, Small Steps 130B and Large Steps 130C. There are respective transitions 130T between these sub-modes. As just mentioned, other basic modes include transition states. For example, referring to FIGS. 3E and 4C, the Ramp Down mode 134, in addition to being divided into sub-modes Ramp Down 134A and Steep Ramp Down 134B, has a transition state Transition Ramp Down 134C to allow definition of intermediate settings of the flexion control devices to provide a smoother transition from the Ramp Down mode 134 to the Normal Walking mode 130, and vice-versa. Transitions normally have associated values which are set by interpolation between the values of the starting mode and those of the finishing mode in each case. Additional Ramp Down sub-modes are provided for slow and fast walking velocities.

Similar sub-modes exist for the Ramp Up mode (see FIG. 3E).

Additional transition states and corresponding actuator settings (i.e. control device settings) are related to each other in further layers (not shown) of the matrix represented by the table of FIG. 4A. For example, getting up from a chair, as illustrated by the Sit-Down-Stand-Up Mode state 155 in the finite state diagram of FIG. 3D, uses a set of output settings from one layer of the matrix and then, moving to the Stand Relaxed mode 157, from another matrix layer, or moving to the Slow Walking mode (a sub-mode 160A of a Velocity mode 160 (in effect walking which is other than normal walking)) require transition states Transition Sit 155A, Stand Up 155B, and Transition Walking (a sub-mode 157C of the Stand Relaxed mode 157) These transitions avoid the need to compensate for or accommodate sudden changes so that the limb operation is as nearly possible seamless and smooth as the amputee moves from one activity mode to the other. Each matrix has a set of relationships associating and linking modes, events and transitions with different control settings for implementation in real time.

The control system open architecture allows the programming of additional matrices, e.g. for defining control functions associated with additional events or activities, as well as integration of additional data streams.

In general, when the control system is operating to indicate a particular activity mode, it will continue to indicate that same mode until it receives a sensor signal which is interpreted as indicating a transition to a different mode.

The settings stored in the matrices described above with reference to FIGS. 4A to 4D, and the settings at other matrix levels (not shown) of the matrix are adjusted to suit the individual amputee during a calibration program mode. A typical calibration routine for establishing the matrix settings includes:—

1. Level walking with different velocities
2. Level walking—starting and stopping
3. Walking up and down a ramp at different velocities and with different gradients
4. Walking up and down stairs
5. Level walking with different disturbances
6. Sitting down and getting up from and to walking and standing
7. Other activity modes The system does allow for calibration on the basis of tests 1., 2., and, preferably, 3. above only, default values for bands of values that are adjusted according to the level walking values being set for activities associated with tests which have not been carried out, e.g. owing to a lack of facilities.

The calibration may be performed by a prosthetist feeding settings to the prosthesis using the user interface 120 (FIG. 2). As an alternative, or in addition, depending on the mode of activity in question, a self-adjustment, self-programming or automatic calibration phase may be included whereby the control system provides a series of trial settings for particular activity modes.

A particular technique used in the calibration program mode of the preferred embodiment makes use of the variation of the shin section bending moment, as sensed by the strain gauges 52, 53 (FIG. 1B) to set plantar-flexion resistance and dorsi-flexion resistance of the ankle flexion control device. In particular, one or both flexion control settings of the ankle joint are modified to achieve a predetermined shin bending moment profile, i.e. the variation of the sensed shin bending moment with time during individual stance phases of the walking gait cycles. Similarly, the ankle joint plantar-flexion resistance and/or dorsi-flexion resistance may be changed in response to the sensed foot angle, as sensed by the angle sensor 87A, 87B (FIG. 1C) at the ankle joint to achieve a predetermined foot angle profile, i.e. variation of foot angle during the stance phase of the walking gait cycle. In some circumstances, the sensed knee angle and foot acceleration may also be used.

FIGS. 5A to 5D indicate typical profiles for the knee angle, the foot angle, the shin section bending moment, and the global foot acceleration during the gait cycle. The horizontal axis in each graph is time within a gait cycle nominated to the value 1, so that the profile begins with heel contact, progresses through the stance phase to push off (at about 0.6), then continues through the swing phase, and returns to heel contact at 1. Each graph has four plots relating to different combinations of plantar-flexion (PF) and dorsi-flexion (DF) resistance settings, as indicated, a higher number designation for the plots representing higher flexion resistance and a lower number representing a lower respective flexion resistance. The applicants have found that the higher the setting for plantar-flexion resistance, the sharper and more peaked is the foot angle profile (see FIG. 5C). In addition, with high plantar-flexion resistance, the area below the foot angle profile plot is smaller. With higher dorsi-flexion resistance, the area below the foot angle curve becomes rounder and larger. Also, the ratio of plantar-flexion resistance to dorsi-flexion resistance affects the symmetry of the curve and its integral beneath it from a normal value up to the peak, and back to the normal value again. The applicants have found that the combinations of plantar-flexion and dorsi-flexion resistance settings which are preferred, in terms of amputee comfort and effort, were PF6 DF6 and PF8 DF4 which, as can be seen from FIG. 5B, produce lower ankle dorsi-flexion amplitude profiles, both in terms of peak dorsi-flexion and the area under the respective part of the angle profile in the stance phase.

The electronic control system, described above with reference to FIG. 2, makes use of the sensed foot angle profile by measuring both peak foot angle and the dorsi-flexion integral in a process similar to that described above with reference to FIG. 3B to achieve the preferred foot angle profile by adjusting the ankle joint control device flexion resistances. Accordingly, if the peak dorsi-flexion of the ankle joint during the stance phase exceeds a predetermined threshold value, or the area (corresponding to the integral) under the dorsi-flexion curve with respect to time during the stance phase exceeds a predetermined area threshold, the plantar-flexion resistance of the ankle flexion control device is increased and the stance phase dorsi-flexion resistance is decreased. Similarly, if these peak and area values are too low, the plantar-flexion and dorsi-flexion resistances are driven in the opposite respective directions.

In the present embodiment, integrals of the foot angle curve (i.e. dorsi-flexion angle of the ankle) are computed as follows:

A first integral, Integral 1, from a first foot angle value up to the peak

A second integral, Integral 2, from the peak down to the crossing of the first foot angle value line again The ratios of Integral 1 to Integral 2 and the sum of the two integrals obtained for different plantar-flexion and dorsi-flexion resistances are typically as shown in Table 1

TABLE 1

|  | Integral 1/Integral 2 | Integral 1 + Integral 2 |
|---|---|---|
| "PF 3 DF 8" | 0.71 | 56.49 |
| "PF 2 DF 2" | 0.83 | 47.9 |
| "PF 6 DF 6" | 0.94 | 44.85 |
| "PF 8 DF 8"[1] | 1.09 | 40.58 |
| "PF 8 DF 4" | 1.2 | 34.19 |

The ankle joint control device resistances are driven to achieve a ratio of Integral 1 to Integral 2 of around 1 when both settings are in an equal range, i.e. bigger than 1 if the plantar-flexion resistance is greater than the dorsi-flexion resistance and smaller than 1 if the dorsi-flexion resistance is greater than the plantar-flexion resistance. The sum of both integrals is larger the larger is the sum of the dorsi-flexion resistance and the smaller is the plantar-flexion resistance. When both plantar-flexion and dorsi-flexion resistance are approximately equal, the lower the settings the larger is the sum.

Accordingly, the system also uses the ratio of different areas beneath the foot angle profile, respectively when the dorsi-flexion angle is increasing and when it is decreasing, as an input variable for setting the dorsi-flexion and plantar-flexion resistances.

Figure 5A:
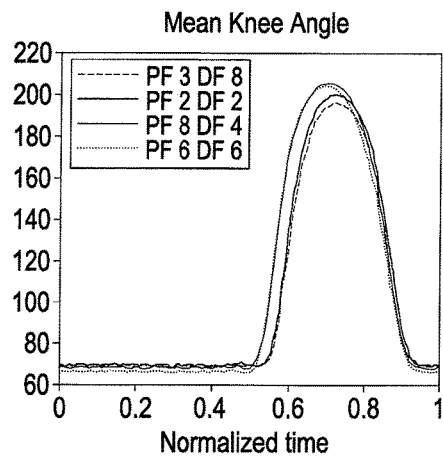
Figure 5B:
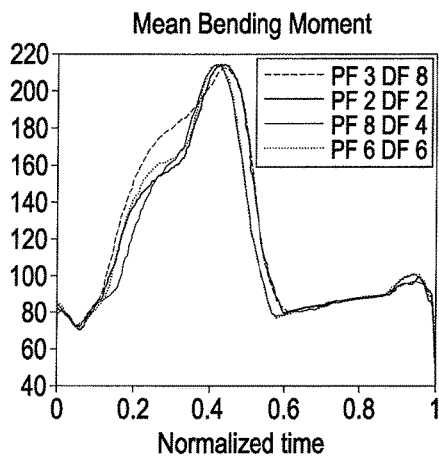
Figure 5C:
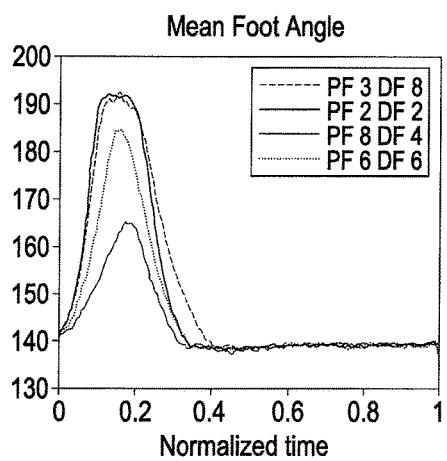
Figure 5D:
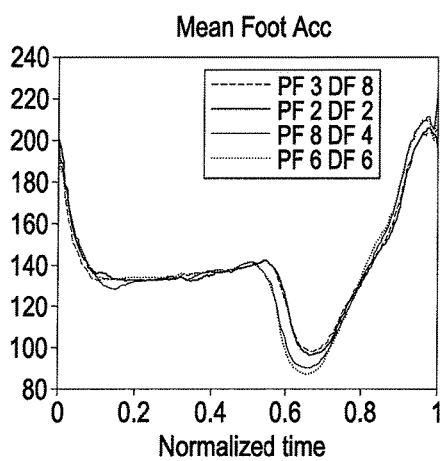

With regard to the shin bending moment profile shown in FIG. 5B, this is significantly affected by the plantar-flexion and dorsi-flexion resistance settings at the ankle joint. With moderately low plantar-flexion resistance and high dorsi-flexion resistance (PF3 DF8), the moment increases rapidly during the early part of the stance phase and then, towards mid-stance, the gradient is relatively small so that the peak moment is relatively late in the stance phase. In contrast, with relatively high plantar-flexion resistance and somewhat lower dorsi-flexion resistance (PF6 DF6), for example, the gradient in the early stance phase is less steep and there is a step in the region towards mid-stance followed by another period of rapidly increasing moment to the bending moment peak. The area under the bending moment curve during the stance phase is affected by these different profiles, as indicated in Table 2 below, which tabulates the ratio of the curve area for the first, second and third resistance combinations shown in FIG. 5B relative to that for the fourth combination, PF6 DF6. (For completeness, similar ratios are tabulated in Table 2 for the foot angle and the ratio between the foot angle and shin bending moment.)

TABLE 2

|  | Foot angle ratio in relation to "PF 6 DF 6" | Bending moment ratio in relation to "PF 6 DF 6" | Ratio between foot angle and bending moment |
|---|---|---|---|
| "PF 3 DF 8" | 1.34 | 1.08 | 0.78 |
| "PF 2 DF 2" | 1.15 | 1.02 | 0.71 |
| "PF 8 DF 4" | 0.83 | 0.93 | 0.56 |

The electronic control system of FIG. 2 computes the shin bending moment area using signals from the strain gauges 52, 53 (FIG. 1B) to provide an input for setting plantar-flexion and dorsi-flexion resistances.

An option in the preferred electronic control system is to divide the sensed shin section bending moment profile before the peak into three periods. Thus, the preferred profile has a first period in which the moment increases with a first gradient, followed by a second period in which the moment increases with a second gradient which is significantly less than the first gradient, followed by a third period in which the gradient reverts to a level similar to that of the first period. This is the profile which the applicants have found is most comfortable for the typical amputee. Iterative adjustments of the stance phase plantar-flexion resistance and dorsi-flexion resistance are made to achieve the preferred profile. The preferred profile is also characterised by the third period being at least 80 percent of the second period, in terms of duration.

In the present embodiment, where the settings indicated by the sensed foot angle are different from those indicated by the sensed bending moment, it is the settings indicated by the bending moment which are given precedence. It is possible, in variants of the invention, to dispense with the sensed foot angle as a control input.

The adjustments in control device settings described above are performed during the calibration program mode so that subsequently, during locomotion, the plantar-flexion and dorsi-flexion resistances are automatically and dynamically set according to activity mode.

The control functions described above with reference to FIGS. 5A to 5D are ones performed during level walking. These functions are performed in the same way when walking up slopes and walking down slopes although, under those conditions, values of the parameters illustrated in FIGS. 5A to 5D are different.

Described above is the stepwise reduction of the knee flexion damping resistance in the Ramp Down mode. Referring to FIG. 6, the variation in the damping resistance at the knee in the Ramp Down mode is illustrated in conjunction with knee angle, shin bending moment, foot angle, and foot acceleration curves. As shown, the flexion resistance 200 is high during the major part of the stance phase. At or immediately after the maximum of the shin bending moment, indicated by the arrow M, the knee flexion resistance is reduced to the intermediate level or an interval which ends at or very shortly after the end of the stance phase indicated by the arrow N, whereupon a further reduction in knee flexion resistance is effected to reduce the resistance level to the low (L) level indicated in FIG. 4C. The flexion resistance reverts to the high level in late swing, to prepare for commencement of the stance phase at heel strike, indicated by the arrow. Actuation of the first step wise reduction in resistance is performed in response to detection of a negative-gradient bending moment, derived from strain gauges mounted on the shin section. The second step wise reduction in flexion resistance is actuated in response to the knee angle reaching a predetermined knee angle threshold in the early part of the swing phase, as sensed, for instance by a piston/senor. Typically, the threshold at which the second step wise reduction in knee flexion resistance is a knee angle of 50 percent of the maximum knee angle achieved during the swing phase. This programmed step wise reduction in knee flexion resistance is not performed in the level velocity or Ramp Up modes. In those modes switching occurs instantaneously between high and low resistance settings towards the end of the stance phase. The duration of the interval during which the flexion resistance is at the intermediate level in the ramp down mode is typically 25 percent of the stance phase duration.

As shown in FIG. 6, and described above with respect to the stepwise changes in resistance, in some embodiments, the damping resistance of the knee flexion control device may be configured to remain at a single, constant resistance level corresponding to the second, intermediate resistance level (M) for a second period of time.

In the preferred embodiment described above, the electronic control system has a master microprocessor controller and two slave microprocessor controllers, one for the knee joint and one for the ankle joint. Alternative arrangements are possible. Indeed, all control functions may be performed by a single microprocessor controller, preferably mounted at the knee level, the single controller collecting data from sensors associated with both joints, as in the preferred embodiment, i.e. from different areas of the prosthesis. The single controller would perform advanced analysis of gait and circumstances (i.e. environment, including ground inclination) based on sensor signals from two or more areas of the prosthesis. Additionally, a single controller would monitor the feedback signals from the knee and ankle adjustment motors rather than having such functions performed by slave controllers.

In a variant of the above-described prosthesis, the electronic control system has a bi-lateral mode to allow intercommunication of two limb prostheses for bilateral amputees. In this case, the user interface 120 (FIG. 2) incorporates a hard-wired interconnection incorporating a UART port for communication with the second prosthesis. A wireless communication port may be used instead. The matrices of FIGS. 4A to 4D are expanded for the bi-lateral mode so that both prostheses are synchronised to provide correct damping levels at the knee and the ankle in each case. The high-yield resistance setting for stance control release is timed to be in phase with the initiation of high-yield resistance in the other prosthesis. Similarly, pneumatic swing controls are also adjusted for different speeds for right and left limbs. Plantar-flexion damping of the ankle is synchronised with dorsi-flexion damping of the other limb to provide natural progression and optimum function.

The invention claimed is:

1. A lower limb prosthesis comprising:
    an attachment section,
    a shin section,
    a foot section,
    a knee joint pivotally connecting the attachment section and the shin section, the knee joint including a dynamically adjustable knee flexion control device for damping knee flexion,
    an ankle joint pivotally connecting the shin section and the foot section,
    a plurality of sensors including an inclination sensor, the inclination sensor for generating inclination sensor signals indicative of ground inclination, the plurality of sensors collectively being arranged to generate sensor signals indicative of at least one of a kinetic or a kinematic parameter of locomotion and of walking environment, and
    an electronic control system coupled to the sensors and to the knee flexion control device in order dynamically and automatically to modify a flexion control setting of the knee joint in response to signals from the sensors,
    wherein arrangement of the sensors, the electronic control system and the knee flexion control device is such that the inclination sensor signals indicating descent of a downward incline are sufficient to cause the electronic control system to set the damping resistance of the knee flexion control device:
        to a first level for a first period of time during a majority of a stance phase of a gait cycle,
        to a second, intermediate, constant, lower level for a second period of time, a beginning of the second period of time occurring during a latter half of the stance phase and an end of the second period of time occurring during a first half of a swing phase of the gait cycle, and subsequently
        to a third, yet lower level, for a third period of time during a majority of the swing phase.

2. A prosthesis according to claim 1, arranged such that the arrangement of the sensors, the electronic control system and the knee flexion control device is such that when the inclination sensor signals indicate level walking or ascent of an upward incline, the damping resistance of the knee flexion control device is switched directly from the first level to the third level.

3. A prosthesis according to claim 1, arranged such that signals fed to the knee flexion control device cause the flexion resistance to be reduced in a step change at an end of the first period of time to the second level, and to be reduced in a step change at the end of the second period of time to the third level.

4. A prosthesis according to claim 3, wherein the step change at the end of the first period of time to the second level is configured to be performed in response to detection of a negative-gradient bending moment in the shin section.

5. A prosthesis according to claim 4, wherein the plurality of sensors comprise strain gauges mounted on the shin section, and wherein the strain gauges mounted on the shin section are configured to detect the negative-gradient bending moment in the shin section.

6. A prosthesis according to claim 3, wherein the step change at the end of the first period of time to the second level is configured to be performed in response to detection of a maximum shin bending moment.

7. A prosthesis according to claim 6, wherein the plurality of sensors comprise strain gauges mounted on the shin section, and wherein the strain gauges mounted on the shin section are configured to detect the maximum shin bending moment.

8. A prosthesis according to claim 1, arranged such that a duration of the second period of time is further at least 10% of a duration of the stance phase.

9. A prosthesis according to 1, arranged such that the second period of time spans a toe-off point at an end of the stance phase.

10. A prosthesis according to claim 1, arranged such that the second period of time begins at a shin bending moment maximum.

11. A prosthesis according to claim 1, arranged such that the second period of time ends after toe-off and as a knee flexion angle is increasing.

12. A prosthesis according to claim 11, arranged such that the second period of time ends when the knee flexion angle has increased to a threshold at between 30 percent and 70 percent of a maximum knee flexion angle achieved in the swing phase.

13. A prosthesis according to claim 1, arranged such that detection of the downward incline causes the electronic control system to enter a ramp down mode and wherein, in the ramp down mode, the electronic control system follows a ramp down resistance program controlling switching of the knee flexion control device from the first level to the second level and from the second level to the third level.

14. A prosthesis according to claim 13, arranged such that a duration of the second period of time is further greater than 15% of a stance phase duration.

15. A prosthesis according to claim 13, wherein the plurality of sensors are collectively arranged to generate sensor signals indicative of at least one kinetic parameter of locomotion and the prosthesis is further arranged such that the switching of the knee flexion damping resistance from the first level to the second level is performed in response to at least one of the measured kinetic parameters.

16. A prosthesis according to claim 15, wherein the at least one kinetic parameter is a shin bending moment.

17. A prosthesis according to claim 13, arranged such that, at the end of the second period of time, the knee flexion damping resistance is switched from the second level to the third level in response to at least one of the measured kinematic parameters.

18. A prosthesis according to claim 17, wherein the kinematic parameter is a measured knee angle.

19. A prosthesis according to claim 1, wherein the knee joint and shin section together form an articulated knee and the foot section and the ankle joint together form an articulated foot, wherein the plurality of sensors comprise at least one sensor on the articulated knee and at least one sensor on the articulated foot, and wherein the electronic control system is coupled to the sensors and to the knee flexion control device in order to dynamically and automatically modify the flexion control setting of the knee joint in response to signals from the at least one sensor on the articulated knee and the at least one sensor on the articulated foot.

20. A prosthesis according to claim 1, wherein in an instance in which the inclination sensor signals indicate a level or ramp up surface, the damping resistance of the knee flexion control device is configured to reduce from the first level to the third level during the gait cycle without being set at the second level for the second period of time.

21. A prosthesis according to claim 20, wherein in the instance in which the inclination sensor signals indicate the level or the ramp up surface, the damping resistance of the knee flexion control device is configured to reduce instantaneously from the first level to the third level.

22. A prosthesis according to claim 1, wherein the first level is constant.

23. A prosthesis according to claim 1, wherein the third level is constant.

* * * * *